(12) United States Patent
Pathak

(10) Patent No.: US 8,298,273 B2
(45) Date of Patent: Oct. 30, 2012

(54) RENEW COMPRESSION SCREW

(76) Inventor: Kartikeya P. Pathak, Ahmedabad (IN)

( * ) Notice: Subject to any disclaimer, the term of this patent is extended or adjusted under 35 U.S.C. 154(b) by 332 days.

(21) Appl. No.: 12/655,670

(22) Filed: Jan. 5, 2010

(65) Prior Publication Data

US 2010/0168802 A1 Jul. 1, 2010

(51) Int. Cl.
*A61B 17/86* (2006.01)

(52) U.S. Cl. .......................... 606/305; 606/54

(58) Field of Classification Search .............. 606/53–60, 606/300, 301, 304–306, 308, 314, 318, 287, 606/292; 411/413
See application file for complete search history.

(56) References Cited

U.S. PATENT DOCUMENTS

| | | | |
|---|---|---|---|
| 2,143,922 A * | 1/1939 | Longfellow | 606/60 |
| 5,300,072 A | 4/1994 | Aghion | |
| 5,540,690 A * | 7/1996 | Miller et al. | 606/287 |
| 5,545,163 A | 8/1996 | Miller et al. | |
| 5,601,558 A * | 2/1997 | Torrie et al. | 606/326 |
| 5,690,633 A * | 11/1997 | Taylor et al. | 606/57 |
| 5,713,903 A * | 2/1998 | Sander et al. | 606/326 |
| 5,720,753 A * | 2/1998 | Sander et al. | 606/104 |
| 5,743,912 A | 4/1998 | Lahille et al. | |
| 5,746,741 A | 5/1998 | Kraus et al. | |
| 5,814,046 A | 9/1998 | Hopf | |
| 5,989,255 A | 11/1999 | Pepper et al. | |
| 6,010,504 A | 1/2000 | Rogozinski | |
| 6,171,307 B1 * | 1/2001 | Orlich | 606/53 |
| 6,210,376 B1 * | 4/2001 | Grayson | 604/264 |
| 6,375,657 B1 | 4/2002 | Doubler et al. | |
| 6,575,976 B2 * | 6/2003 | Grafton | 606/916 |
| 6,623,492 B1 * | 9/2003 | Berube et al. | 606/151 |
| 7,641,677 B2 * | 1/2010 | Weiner et al. | 606/315 |
| 7,666,212 B2 * | 2/2010 | Pathak | 606/304 |

* cited by examiner

Primary Examiner — Pedro Philogene
(74) Attorney, Agent, or Firm — Clifford W. Browning; Krieg DeVault LLP

(57) ABSTRACT

An external fixator implant screw with an intercalated head, of which one embodiment for lag screw mode has a spherical head, and a partial thread. The spherical head in countersunk bone exerts concentric wide contact on insertion at various angles to surface. Optional canalization of central rod allows guide wire technique and optional mobility of head allows variable shaft length between head and thread. Another embodiment for use in basic implant mode, in a single bone fragment, at right angles to bone surface, has a conical head with limited basal contact on bone, the head being integrated to a solid rod and is fully threaded from head to leading tip. In both embodiments, the load transmission is renewable from outside in case of loosening, without reopening any wound. The implant is made of biocompatible material.

1 Claim, 9 Drawing Sheets

TAYLOR ET AL.

PRIOR ART, TAYLOR ET AL.

RENEW COMPRESSION SCREW

"The Renew Compression Screw", is a basic bone implant for external fixator, of an improved and renewable stability; and also is a lag screw with renewable compression on better mechanical principles, resulting in a durable biomechanical condition for bone union.

CROSS-REFERENCE TO RELATED APPLICATIONS

"Not applicable"

STATEMENT REGARDING FEDERALLY SPONSORED RESEARCH OR DEVELOPMENT

"Not Applicable"

REFERENCE TO A MICROFICHE APPENDIX

"Not Applicable"

BACKGROUND OF THE INVENTION

This relates to the field of Orthopaedics and Trauma, human or veterinary. It can be used for other biological fixations/immobilizations such as botanical or other forms of life and for tissues other than bone. It can be used in any engineering or mechanical endeavour in which it serves to hold and/or compress together fragments or masses of material together, while taking part in an outside construct at a distance from the fragments. Bone is living tissue. Bone fragments and surfaces can unite by biological activity over a length of time, given proper conditions to favor it. During this biological process of healing, the fragments have to be held together continuously by various means, to achieve a finally acceptable result for restoring function to the part. The biological process is favoured by the following measures.
1. Immobilization of the fragments or surfaces attempting union.
2. Compression of the surfaces to increase the rigidity of immobilization, and also promoting the biological process of direct union without excessive callus formation.
3. Relieving recurrent stress and injury to the soft tissues and neuro-circulatory mechanisms by immobilization.
4. Immobilizing only the healing parts, while encouraging movement and activity of un-injured parts.

This has been attempted by the following methods.
A. Continuous traction
B. External casts of Plaster of Paris, other casting materials and bracing.
C. Internal fixation.
D. External fixation.
E. Combined methods of fixation.

A. Continuous Traction:

This can restore the length of the limb, and further measures can correct rotation and angulation to an extent.

The following problems of this method seldom make it the preferred treatment.
1. It is difficult to maintain the traction force continuously even with very frequent attention.
2. Patient cooperation is difficult to achieve.
3. Due to intermittent loss of traction force, malunion may occur. Distraction and movement of fragments may cause delay or failure of union.
4. Circulatory problems can occur in the distal limb.
5. Wounds in the traction surface will not allow such treatment.

B. External casts of Plaster of Paris, Other Casting Materials and Braces.

The following problems are associated with them.
1. The immobilization is not rigid enough, when this is critically essential.
2. Encircling of the part causes sweating and discomfort in hot climates.
3. Pressure sores can occur at pressure points, or due to insertion of hard objects by patient for scratching. Bugs can get in.
5. Swelling of part within the cast can cause tightness and loss of circulation or nerve function.
5. Loosening of cast occurs due to loss of swelling of the part, or due to reduction of the thickness of the padding by moisture, resulting in loss of reduction.
6. There is no access to any wounds inside, which may need regular attention, except by cutting out windows or leaving the cast incomplete, which may jeopardize the immobilization, and fracture position.
7. Uninvolved parts also are immobilized, a setback to recovery.

Due to these factors it can suffice only when rigid immobilization is not critically important, and usually in the absence of complicating factors of wounds and circulation.

C. Internal Fixation:

This may be applied along the side of a bone in the form of a plate and screws of any preferred design. It allows accurate reduction when this is most desirable; a bone graft can be added and lag screws driven as often as feasible, for inter-fragmentary compression. Sliding devices can be added to passively close any gaps arising later.

Disadvantages are as under:
a. Large exposures are required with relatively greater damage to the soft tissues and bone circulation. Meticulous technique may minimise this, yet the exposure is larger.
b. Compression between fragments once applied at operation wears off within hours, depending on the quality of bone. There is no possibility of renewing this compression once the wound is closed over the device. It is not acceptable to re-anaesthetise and re-expose the device repeatedly to re-tighten the screws.
c. Minimally invasive methods are performed through smaller incisions but in order to place the plate directly on bone, the periosteum and muscle have to be stripped blindly. The plate is always unavoidably placed over some soft tissues, which melt away under the pressure and loosen the plate. Loss of torque of screws is unfavourable to biology of bone healing.
d. Plates are seldom favoured in compound fractures.
e. Fracture haematoma gets dispersed.

Internal fixation may be applied inside the medullary canal of bone in the form of nails, pins and wires.

In closed nailing, the fracture haematoma is preserved.

The disadvantages are as under.
1. It is generally not applicable to children, due to growth plates at the ends of bones.
2. It invades and occupies the bone from end to end, with the possibility of spreading infection.
3. It is not stable to rotational forces, and interlocking methods are not available for all situations.
4. In open nailing, the fracture haematoma is dispersed.

D. External Fixation:

This is most suited for open injuries of bone. The commonly used basic bone implant for the external fixator is the Schanz screw which can be inserted at a safe distance from the open wounds and fracture ends.
1. Access to wounds for frequent attention is easy.
2. There is no aggravation of injury to bone or soft tissue.
3. Safe corridor entries of screws prevent injury to neurovascular structures.
4. In transverse fracture patterns, some compression can be applied along the axis of the bone by dynamizing the construct.

The following limitations remain:
1. The basic implant e.g. the Schanz screw has a tendency to loosen in bone, leading to instability and a proneness to infection. Radial preloading of the implant in bone improves the stability, by the technique of inserting a larger diameter screw in a suitably smaller diameter drill hole, but the rod/bone interface remains small.
2. The preload is only in one mode, viz. Radial, over a small area.
3. After loosening, there is no way of regaining any degree of stability in the same position, before the onset of infection. If the loose screw had been initially placed in a mechanically ideal site, then any next site for repositioning will be less than ideal.
4. There is no lag screw effect of a Schanz screw, to exert inter fragmentary compression. Inter-fragmentary compression greatly enhances the stability, as well as the biological process of union. Fragments can at most be splinted across, but not drawn together and compressed in the lag screw mode, by the conventional Schanz screw.
5. Taylor et al had patented a lag screw external fixator implant with intercalated heads of various shapes, meant for compression of fragments. All the heads patented by them had engagement surfaces which were flat, their plane being at 90-degrees to the rod axis. Unless such a device is always driven at 90-degrees to the bone surface, the head will stand up on edge, with too much stress concentration at a point, leading to crumbling of bone and loosening.

Also, two fracture surfaces are best compressed by a lag screw driven at 90-degrees to the fracture plane and not at 90-degrees to the outer surface.

Since fracture planes run across a bone, they are at various angles to the outer surface of bone and not parallel to it.

In actual use, the devices of Taylor et al would not be at 90-degrees to the outer bone surface, being required to be at 90-degrees to the fracture plane. This would make the engagement surface of head stand up at an angle to the surface leading to mechanical failure and loosening. This may be the reason, why the device did not gain wide acceptance amongst those skilled in the art, and for the paucity of any reports on its use in English literature.

If compression were applied at 90-degrees to outer bone surface, but not at 90-degrees to fracture plane, it will not only be inefficient but may actually make the fracture surfaces to slide upon each-other rather than be compressed.

Taylor et al suggested that their device might also be used as "traditional external fixator" screw, in which case the head may be allowed to stand away from the bone surface, without engaging or loading the bone surface.

For such use as a "traditional" device, it must be considered that an intercalated head adds to the cost of the implant and needs a little larger entry incision. Unless the head is going to do some work, the surgeon skilled in the art will not use it, preferring a conventional implant widely available, rather than pay for an intercalated head and not put it to use. This could have ruled out its acceptance even as a conventional implant.

Taylor et al thus did not provide for the need of inserting a lag screw device at different angles to the outer surface of bone, which is the crux of the art of lag screw fixation.

Taylor et al do not mention a spherical shape in their claims or any part of text, nor does their discoid head with rounded edges stand up to a close geometric scrutiny for being "spherical on account of being a segment of a sphere". In a similar way, none of the heads claimed by Taylor et al satisfy the criteria of being "conical", when scrutinized geometrically. They describe a "Gemini capsule" shaped head at their FIG. 6. This head they refer to as being "conical" on one occasion at column 7, lines 32-34 of their application. This Gemini capsule head is in fact quite pear-shaped, and unlike any geometrical cone.

Ignoring Botanical interpretations of the term Cone, a Cone has been defined at Merriam Webster Online Dictionary as:

"A solid generated by rotating a right triangle about one of its legs—called also a right circular cone." Or "A surface traced by a moving straight line passing through a fixed vertex." Or, "A solid bounded by a circular or other closed plane base and the surface formed by line segments."

"The "Gemini capsule" shape head seen at FIG. 6 of their patent has a narrower base which soon expands to a low belly in a curved line and then tapers to the vertex. Geometrical cones are widest at the base, tapering in straight lines to the vertex in ever reducing cross-sectional areas, without any widening from base upward. If curved lines are allowed in the geometry of a cone as in the Gemini capsule, with expanding and reducing cross-sections, then bizarre shapes can compete for the definition of a cone. The preferred conical head therefore as claimed in this application for a basic implant, is not anticipated by any device of Taylor et al, who claim only a lag screw device and not a basic implant.

E. Combined Methods of Fixation:

When any one method is inadequate to neutralize all the forces of muscular pull and gravity, another method is added onto the first. For example, in "mini-cum-external fixation" methods; one or two lag screws used to hold together some fragments, are supplemented by an external fixator construct, or by traction.

Even with such a supplementation, the lag screws can fail, because by the blind stab-hole technique of insertion, there is always some interposition of soft tissue between the screw head and the bone surface. This soft tissue quickly undergoes pressure necrosis to loosen the compression by loss of torque. The only residual control is the external fixator, which may not be adequate for the situation. The compression once lost cannot be regained.

SUMMARY OF THE INVENTION

The invention is aimed at preserving and augmenting the functions of the primary bone implant of the external fixator in which, Axial and Surface preloads are added to the older method of Radial preloading of the implant in bone. This has an added effect on the stability and durability of the implant. The former two preloads are also renewable, because the screw can again be tightened after the first insertion. The triple preload widely distributes stresses away from the interface of rod/drill hole, where loosening of a conventional implant occurs.

Another embodiment is a lag screw, which can be driven at a mechanically sound right angle to the fracture plane, with renewable compression. Renewed and prolonged inter-fragmentary compression by external fixator is a new advantage to the biology of bone healing.

This implant can also be used to supplement minimally invasive plate osteosynthesis with double advantage. The torque can be renewed to keep plate firmly on bone and the same implant can form an outside construct to augment the stability of an implanted plate. All positive features of the prior implants are retained; permitting wound access, minimal incisions, safe corridor insertion, soft tissue preservation, and no lengthwise invasion of medullary canal of bone. No novel disadvantages are introduced.

DETAILED DESCRIPTION OF THE INVENTION

Figure 1:
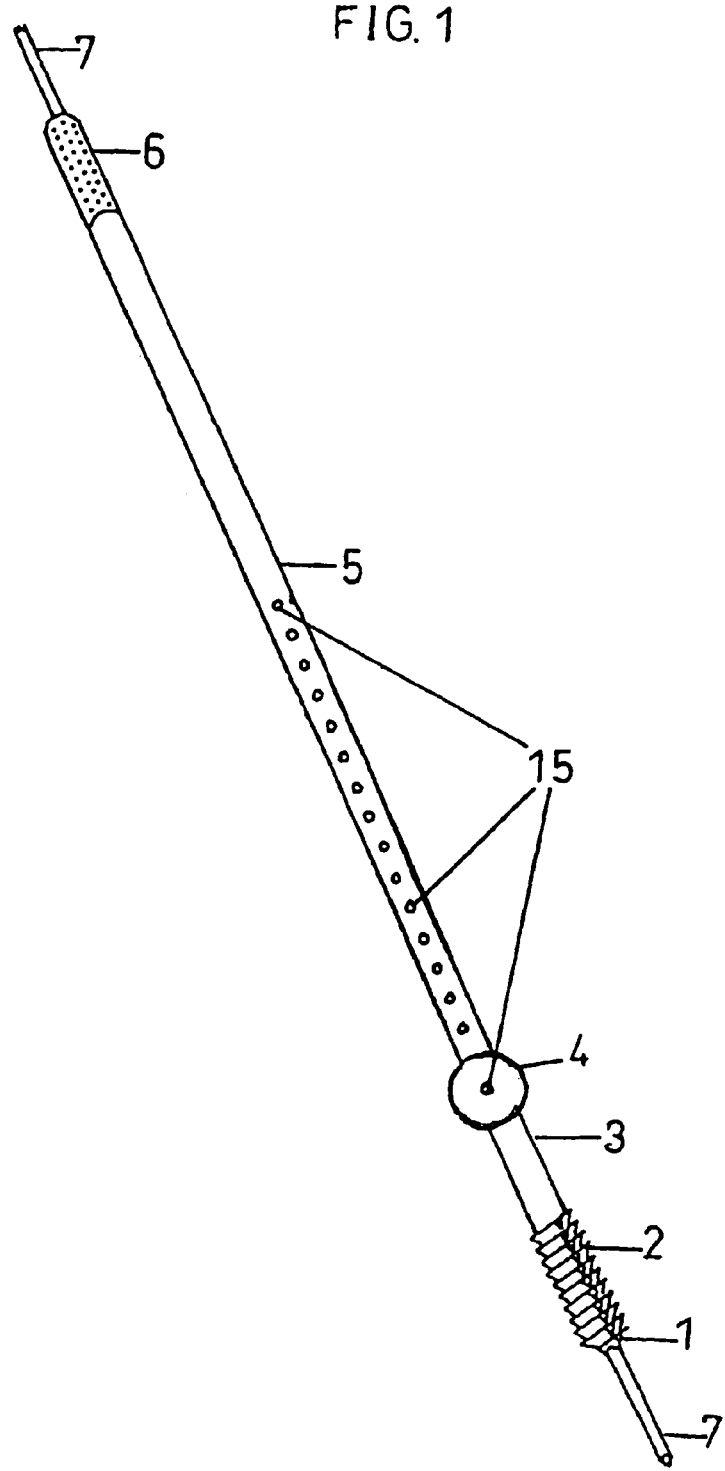
FIG. 1 is a diagrammatic front elevation of the invention with lag screw capability, showing components.

FIG. 1 is one embodiment of the lag screw implant. In the lag mode it is mainly in tension along its axis and other force vectors are neutralized by the basic construct. It comprises:

1 being the tip at the first end, with guide wire 7 in the central canal. The tip shown is self tapping, but optionally a non-self tapping tip may be used.
2 is the short threaded section at the first end, the thread not extending to the head 4.
3 being the smooth screw shaft section meant for gliding through the drill hole in the fragment nearer to head, allowing lag screw compression.
4 is the spherical head for engaging a countersunk surface of the fragment nearer to head. The head may be integral with the rod or may be mobile for fixation at a desired level to rod 5.
Such refixation is provided by means of a transverse screw through the head and drive shaft possessing holes 15, at intervals for screw passage.
5 is the unthreaded drive shaft, which serves for driving the device in or out, also for being secured to an external fixator construct through a clamp; as well as for subsequent turning of device to renew the torque, in case of loosening. It has transverse holes 15, at intervals to accommodate a screw through a mobile head for refixation of head. The holes may be spirally arranged, instead of linear as shown.
6 is the second end which is outside, with a means for gripping, shown as a milled surface in the figure. The grip can optionally be quick coupling, or faceted by triangulation, to suit the gripping handle or chuck.
7 is the guide wire passing from any one end, through the'entire rod and out at the other end. It helps to direct the device at the best angle across the fracture plane.

Figure 2:
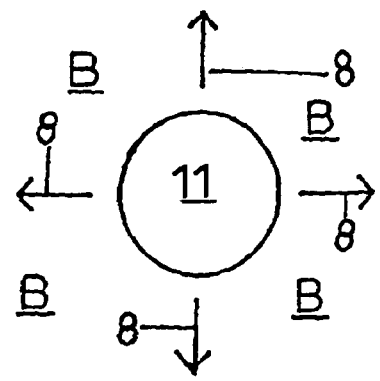
FIG. 2 is a cross section of the prior art basic external fixation implant in bone, showing Radial preload.

FIG. 2 shows the cross-section 11 of a prior art Schanz screw driven into a drill hole of a suitably smaller diameter, in bone B. This generates a Radial preload 8 at the implant/bone interface. Such a preload should not be excessive as judged by those skilled in the art, otherwise micro-fractures in the drill hole wall will occur, with quick loosening.

Figure 3:
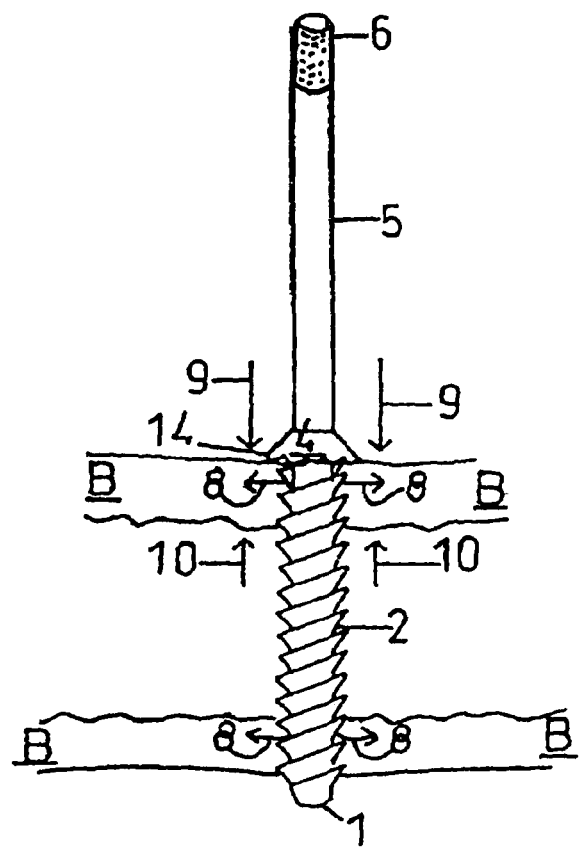
FIG. 3 is a front elevation of the preferred basic external fixation implant in bone, showing the Surface preload and Axial preload in addition to the conventional Radial preload, widely distributing stress over bone/implant interfaces.

FIG. 3 shows the preferred basic implant inserted in bone B. It is for gripping a fragment, not for lag-screw mode.

1 is the non-self tapping tip at the first end. Pre-tapping the thread with tap is known to prolong the durability of a screw against loosening.
2 is the fully threaded section from the first end to the head, providing maximum interface with bone.
4 is the conical head with base towards the bone, with a blunt serrated basal surface for making blunt limited contact on bone at 14. The head exerts a Surface preload 9 on bone surface and on tightening the screw the implant is Axially tensioned in direction shown at 10, within the bone B. The vertex of the cone where the cone converges to a point, is incorporated in the shaft, as the conical head is fixed to the shaft and is continuous with it.

When it became known that bone plates in intimate contact with bone surface interfere with the surface nutrition, limited contact plates were designed with better results. The same principle had not been applied to screw heads. Now, to allow blood supply to reach the drill-hole margin under the conical screw head, a limited contact surface is incorporated where it engages the bone surface, in the preferred device. Sharp serrations are avoided, to prevent too much stress concentration on bone. Nutrition favours bone integrity.

The two preloads, Surface 9 and Axial 10, are in addition to Radial preload 8 of prior art.

The head is integral to the rod for stability, disallowing any micro-movement.

Basic implants are driven at right angles to bone surface, in a single fragment, when the leading base of the head 4 makes all round even contact on bone B.

The device is not canalised, for greater strength against lateral bending.

Figure 4:
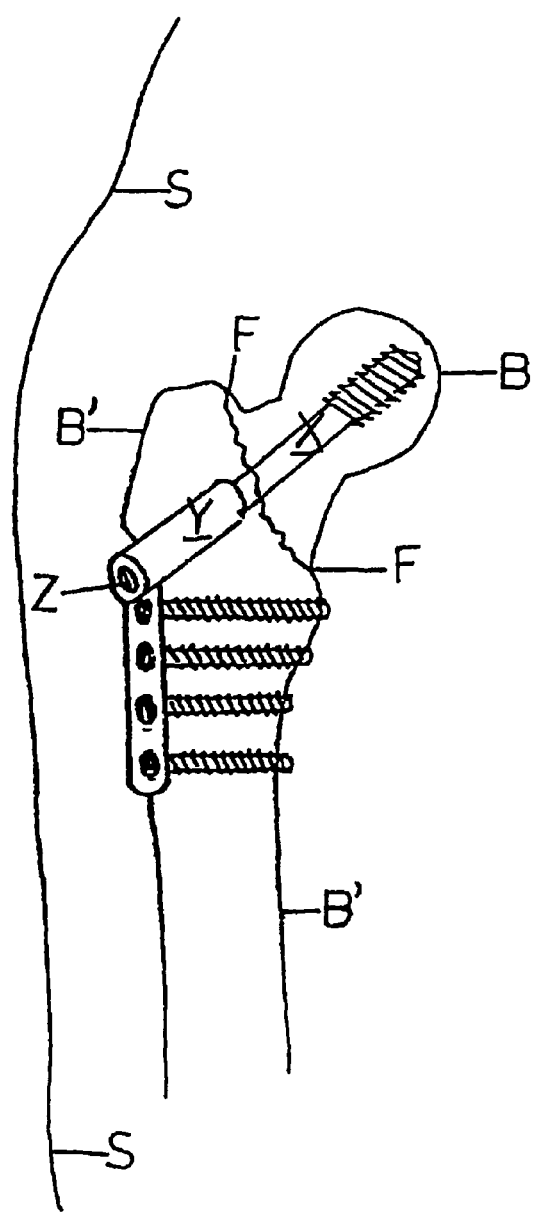
FIG. 4 is the coronal plane view of a prior art two-piece internal fixation device commonly used to fix a proximal femoral fracture and having a screw capable of sliding within the barrel of an angled plate.

The overall dimensions of the device and its parts are made to suit the size of bone, the size of fragments and the depth of bone from skin. Thus in a superficial bone like the tibia, the conical head will be squat, to contain it within the skin. In a deeper bone like the femur the cone will taper taller, for easy removal by spreading the soft tissues. FIG. 4 shows a common variety of hip fracture with fracture plane F, giving rise to two fragments B and B'.

A frequently used two-piece device, a sliding hip screw X in barrel Y, is holding the fracture reduced and compressed by screw Z at the time of operation.

This compression wears off in time after the skin S is closed, with no possibility of recompressing. The screw may fail to slide causing a persisting gap and non-union.

Figure 5:
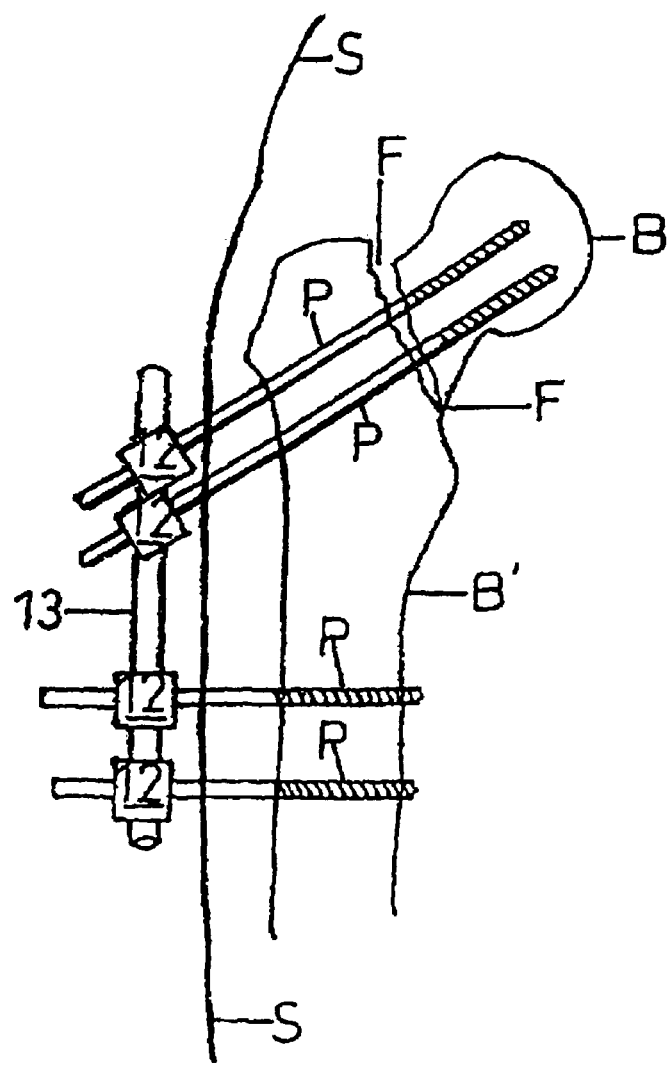
FIG. 5 is the coronal view of prior art external fixator holding the same fracture as in FIG. 4. There is no compression of fracture surfaces. Finer detail of construct is omitted.
Figure 6:
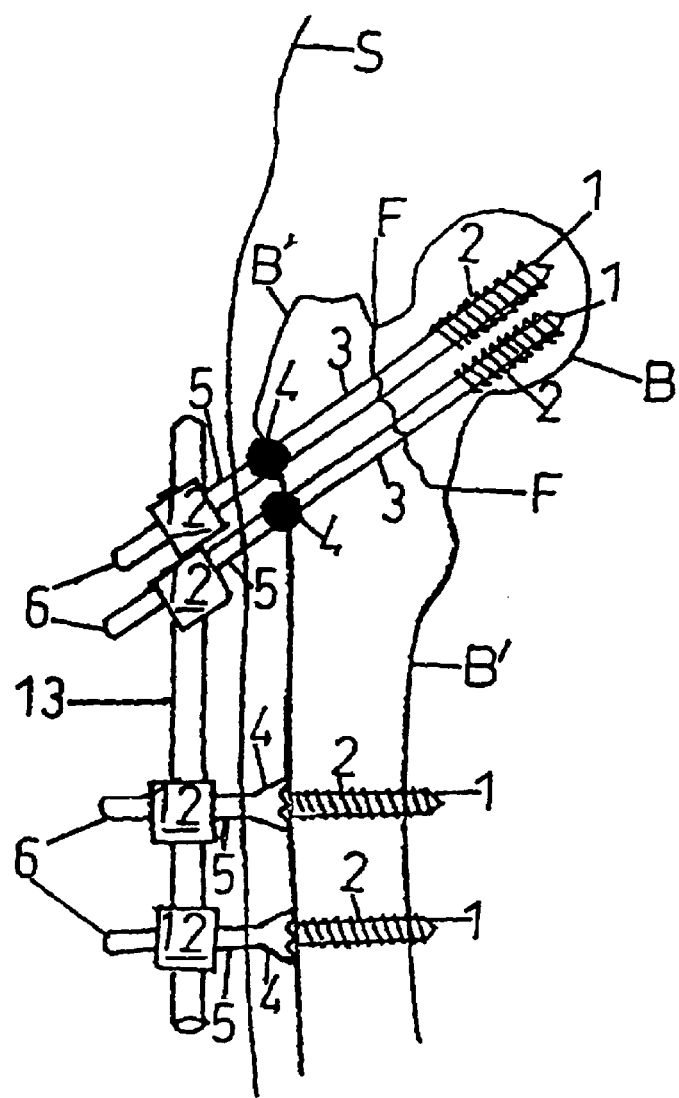
FIG. 6 is the coronal plane view of the same fracture showing the preferred lag screw device at right angles to the fracture plane for efficient compression. Both the lag screws are connected to the two preferred basic implants below, through a construct of clamps and tubes. Finer detail of construct is omitted.

FIG. 5 is the same fracture F as in FIG. 4, held with prior art external fixator comprising pins P, clamps 12 and tube 13. The Fragments B and B' are splinted over the upper two Schanz screws, but no-compression can be achieved, because fragment B' can slide out on the smooth pin section. The lower two Schanz screws are the basic implants, which can be inserted with Radial preload. When Radial preload tapers off, it cannot be renewed unless screw is reinserted at a new site. No other preloads are possible in this prior art design. Persisting gap at fracture site may lead to delay or failure of union. FIG. 6 is the same fracture F between B and B', stabilized with an external fixator using the preferred device. The upper two screws in lag mode help active compression at fracture site, which can be renewed by loosening one screw at a time at the clamp, turning it tighter, and retightening the clamp. The lower two screws are the basic implants for completion of the construct, driven with Radial preload. The head exerts Surface preload on the bone, adding to the lateral stability of the implant. In addition, there is an Axial preload created along the length of the screw, tensioned on driving it tight. These preloads are same as shown in FIG. 3. Thus, there is a wider distribution of stresses compared to the prior art Schanz screw in which all stress is borne at the rod/drill hole interface. The axial and surface preloads are renewable at intervals, without any repeated anaesthesia or exposures. The preloads are also mutually protective. Clamps 12 connect to tube 13.

Figure 7:
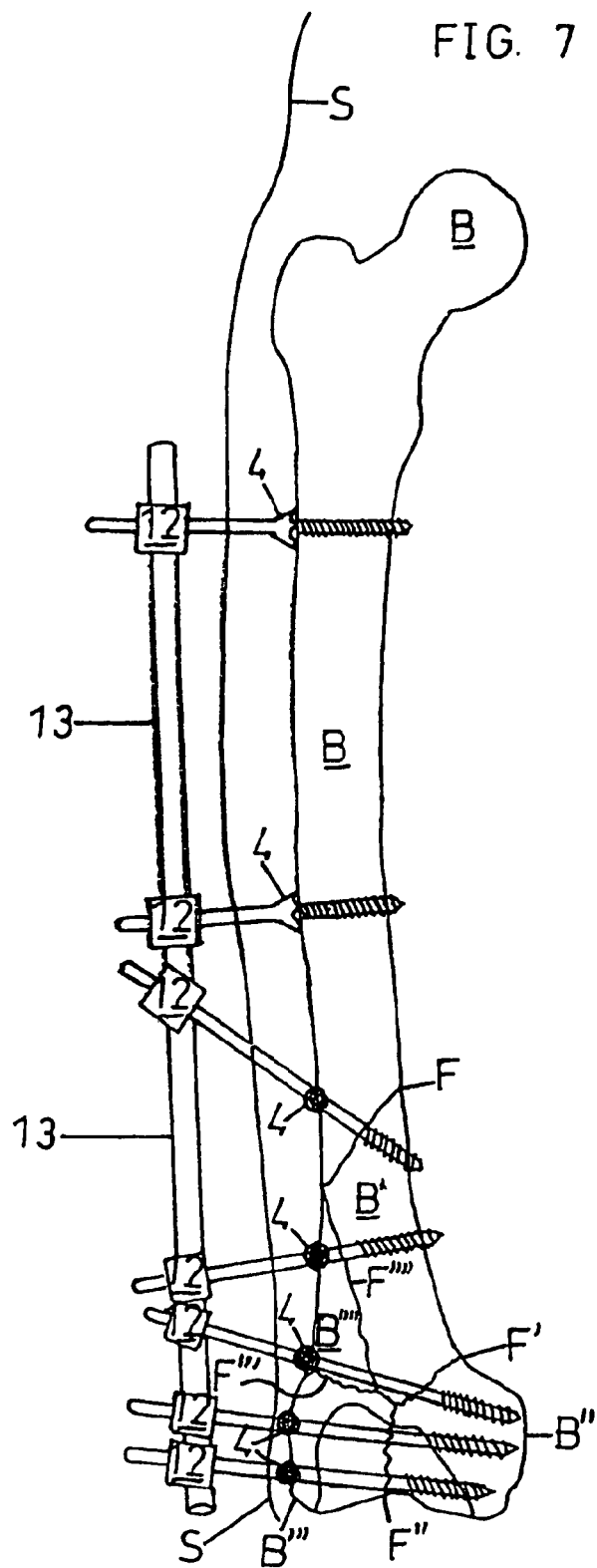
FIG. 7 is a multiple fracture of distal femur involving the knee joint. All fracture surfaces are compressed by preferred lag screws at right angles across the fracture plane. An exception is the third from below, which is compressing three fragments across two fracture planes and cannot be at best angles to both fractures. Two basic implants are holding the proximal fragment, connecting the smaller distal fragments to the rest of the bone. Finer detail of construct is omitted.

FIG. 7 shows a multiple fracture in the lower one third of the femur, involving the knee joint, reduced and held by a fixator using the implants of invention. The fragments are B, B', B", B''' and B''''. The fracture planes are F, F', F", F''', F''''; of which F'' involves the joint surface.

Figure 9:
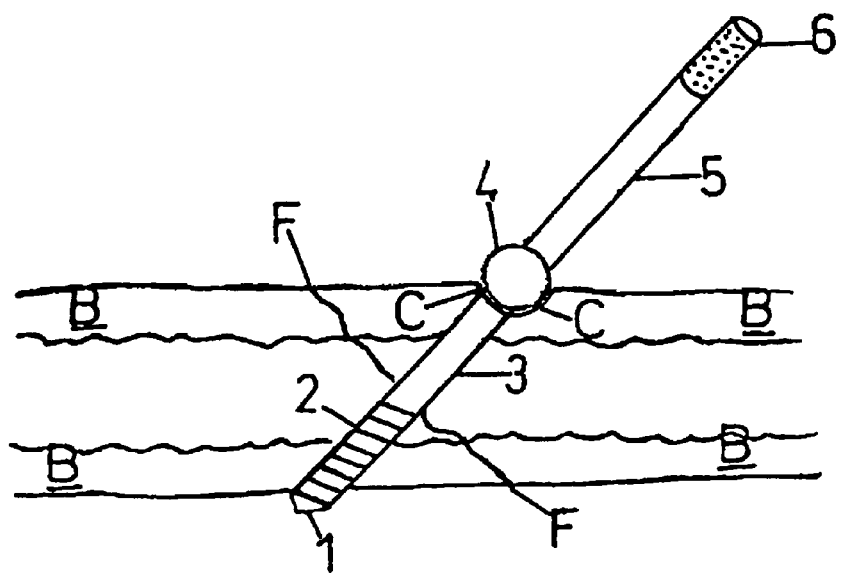
FIG. 9 shows the preferred device driven at 90-degrees to fracture plane, with the Head 4 being a sphere, making wide concentric contact in countersunk bone surface.

The lower five implants are in lag mode, the partial thread engaging only one fragment near the first end. The lag screws are at right angles to the fracture planes, except the third from below. Since this is compressing three fragments B'''', B' and B'' across two fractures F'''' and F', it is at best possible angle that the situation permits. The detail of the head and countersink are shown at FIG. 9.

The upper two implants are in basic mode to control B, the upper two-thirds of the bone. They are at right angles to the bone surface for best mechanical advantage. All implants are connected through clamps 12 to the tube 13.

All the implants have capability of renewable stability and compression, which gives quicker union. This protects against instability, biological failure, and sepsis. The lowest two lag screws compress the articular fragments B" and B''' to each other and stabilize them to the rest of the bone. The screws need not all be in the same plane as shown in the figure. They may tilt into different planes and require creative interconnection to other construct components.

Figure 8:
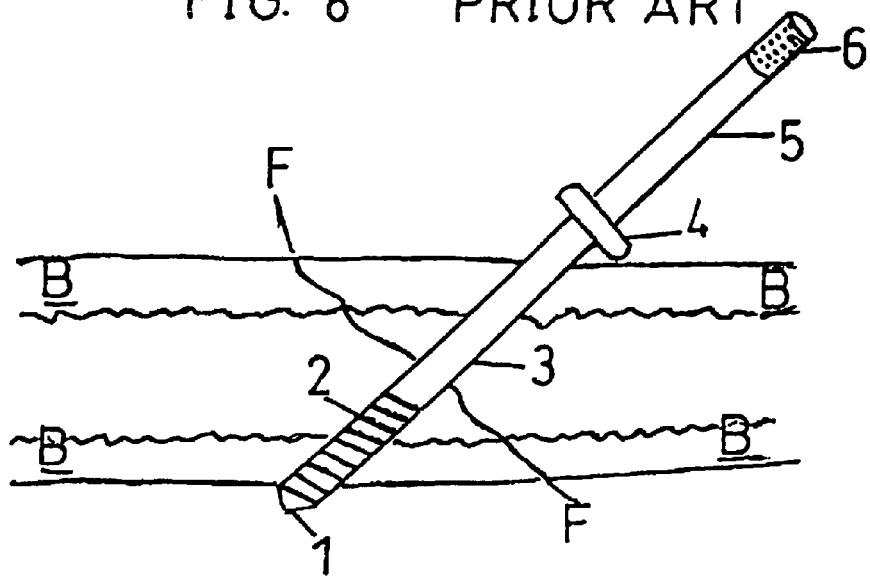
FIG. 8 shows prior art device of Taylor et al driven at 90-degrees to fracture plane for best compression. This makes the head stand on edge, on the surface of bone.

FIG. 8 shows one prior art device of Taylor et al seated in bone B. The fracture plane F runs at about 45-degrees to the outer surface of bone. For optimum compression, the force vector should be at 90-degrees to fracture plane. When their device is so driven, the head 4 gets tilted, being flat at the engagement surface. This leads to much localized pressure on a small area and will lead to mechanical failure of bone by micro fractures. Taylor et al have patented heads of many shapes, all of which have the same flat engagement plane to engage the bone surface.

FIG. 9 shows the preferred lag screw device with a sphere-like head 4, driven at 90-degrees to fracture plane F. Being tilted at about 45-degrees to the surface, it still has a wide concentric contact with the countersink in bone. Wide distribution of compressive load of sphere-like head reduces likelihood of mechanical failure of bone.

Figure 10:
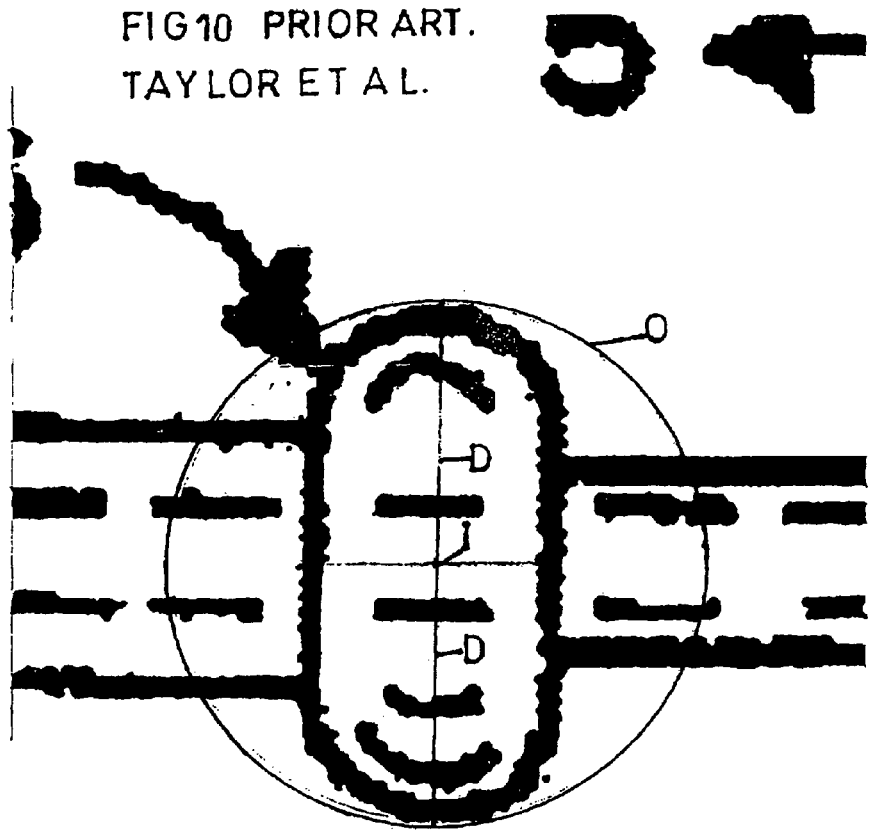
FIG. 10 shows an undistorted enlargement of one prior art head of Taylor et al, for geometrical detail.
Figure 11:
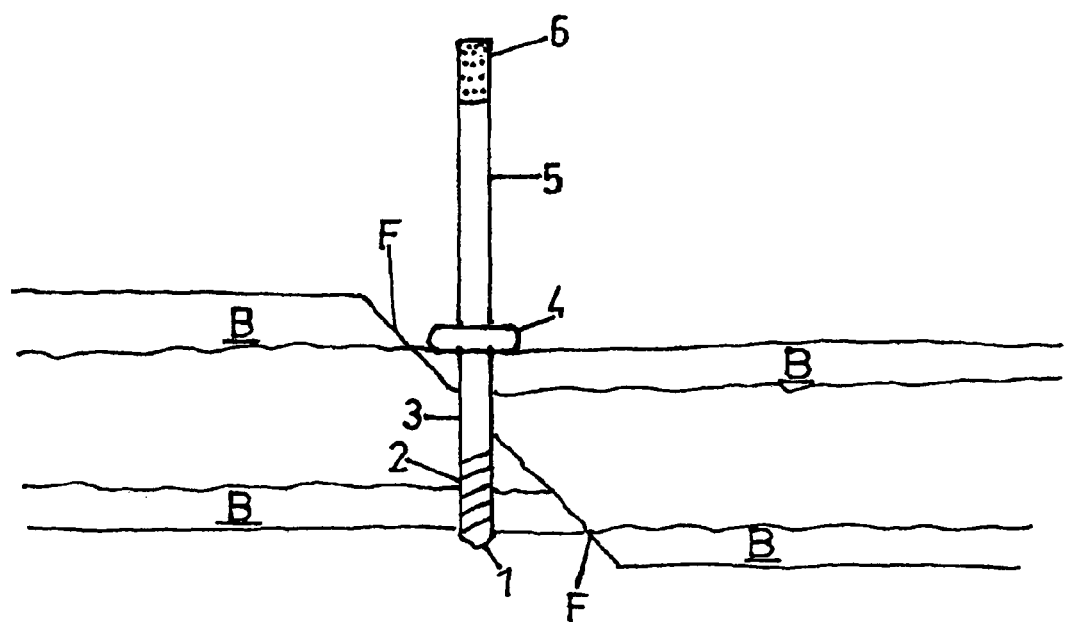
FIG. 11 shows how applying compression to fracture surfaces not at 90-degrees to fracture plane may make the surfaces slide, instead of being compressed.

FIG. 10 shows an undistorted enlargement of the head of Taylor et al, which appears in FIG. 4 of their application. Enlargement has rendered more noticeable the smaller irregularities of the original drawing but the geometry is preserved.

The head, when examined for attributes of being spherical, may vie for the category of "spherical, being a segment of a sphere enclosed by two parallel planes". The two parallel planes of the head being equal, they must lie at equal distance on either side of an equatorial plane of the original sphere, the segment in question being bisected lengthwise by the diameter of the parent sphere/circle.

The diameter of the original sphere from which the segment is derived, would then be the diameter of the segment. If a circle O is described with its centre I and diameter D the same as that of such a sphere segment, then this circle should represent the original sphere from which the segment is derived. The surface of the sphere and the peripheral curve of the segment should then exactly coincide. This is not the case with the head under scrutiny. The curved periphery of the head is part of a much smaller circle/sphere than the curvature of the circle/sphere from which it should have been derived.

The head can then at best be described as "discoid, with rounded periphery" rather than as "spherical, being segment of a sphere". This prior art therefore does not qualify for anticipating the present claim of a device, with spherical head shaped like a sphere. Even if it had qualified for the definition of being spherical, being a segment of a sphere, different segments of a sphere will have such varying mechanical attributes, that many other claims would still be admissible depending on how the segments are derived and what are their engagement surfaces. Different segments of the same sphere can look and mechanically function very differently. It can only be a proper sphere like the preferred head, which can present the same spherical surface all round, with the same mechanics all round. The segments of that do not share all qualities of a sphere.

FIG. 12 shows compression applied to fracture surface of bone B not at 90-degrees to fracture plane F, but at 90-degrees to the outer surface of bone. The fracture surfaces are sliding instead of being compressed.

I claim:

1. A basic mode solid rod external fixator half-pin implant for driving at right angles to bone surface for controlling a single fragment; comprising, a first end for driving in bone, with a thread at first end; and a second end for securing to external fixator by clamps, with a grip for turning at second end;

an intercalated fixed conical head with base towards the first end, having a blunt serrated margin for limited contact on bone surface; the implant device, being fully threaded from first end to intercalated head for wide load bearing, and having an extended rod length from head to the second end for driving, and for securing it to external construct and to renew the stability on loosening.

* * * * *